(12) United States Patent
Dixon et al.

(10) Patent No.: US 9,700,247 B2
(45) Date of Patent: Jul. 11, 2017

(54) PATIENT SUPPORT APPARATUS WITH REDUNDANT IDENTITY VERIFICATION

(71) Applicant: Hill-Rom Services, Inc., Batesville, IN (US)

(72) Inventors: Steven A. Dixon, Cincinnati, OH (US); David L. Ribble, Indianapolis, IN (US); Todd P. O'Neal, Fairfield, OH (US); Christopher K. Lack, Milan, IN (US); James M. Allen, Batesville, IN (US); Thomas F. Heil, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 633 days.

(21) Appl. No.: 13/796,697

(22) Filed: Mar. 12, 2013

(65) Prior Publication Data

US 2013/0253291 A1 Sep. 26, 2013

Related U.S. Application Data

(60) Provisional application No. 61/613,961, filed on Mar. 21, 2012.

(51) Int. Cl.
*A61B 90/96* (2016.01)
*A61B 5/1455* (2006.01)
(Continued)

(52) U.S. Cl.
CPC .......... *A61B 5/14552* (2013.01); *A47C 21/00* (2013.01); *A47C 21/08* (2013.01);
(Continued)

(58) Field of Classification Search
CPC ..... A61B 90/96; A61B 90/98; A61B 5/14552; A61B 5/1172; A61B 5/7495;
(Continued)

(56) References Cited

U.S. PATENT DOCUMENTS

| 4,044,286 A | 8/1977 | Adams et al. |
| 4,506,569 A | 3/1985 | Brown et al. |

(Continued)

FOREIGN PATENT DOCUMENTS

| EP | 2438897 A2 | 4/2012 |
| WO | 2007075701 A2 | 7/2007 |
| WO | WO 2007075701 A2 * | 7/2007 |

OTHER PUBLICATIONS

European Search Report for European Application No. 10174022. 3-1257, Dec. 23, 2010, 5 pages.
(Continued)

*Primary Examiner* — Michelle L Le
(74) *Attorney, Agent, or Firm* — Barnes & Thornburg, LLP

(57) ABSTRACT

A patient support apparatus includes one or more readers and/or sensing devices to receive data that can be use to verify the identity of persons or objects, such as patients, caregivers, and medications. The sensing devices may include, for example, a biometric sensor, a physiological sensor, a bar code reader, a camera, a microphone, or a combination thereof. The patient support apparatus may use identity verification information obtained from these devices for a number of different purposes, including, for example, managing the delivery of therapy, medication, or treatment to a patient associated with the patient support apparatus.

23 Claims, 7 Drawing Sheets

(51) Int. Cl.
| | | |
|---|---|---|
| A61G 7/018 | (2006.01) | |
| A61G 7/05 | (2006.01) | |
| A47C 21/00 | (2006.01) | |
| A47C 21/08 | (2006.01) | |
| G06F 19/00 | (2011.01) | |
| A61B 5/00 | (2006.01) | |
| G06Q 50/22 | (2012.01) | |
| A61B 90/98 | (2016.01) | |
| A61B 5/1172 | (2016.01) | |

(52) U.S. Cl.
CPC ........ *A61B 5/14551* (2013.01); *A61B 5/7495* (2013.01); *A61B 90/96* (2016.02); *A61B 90/98* (2016.02); *A61G 7/018* (2013.01); *A61G 7/0507* (2013.01); *G06F 19/3406* (2013.01); *G06F 19/3462* (2013.01); *G06Q 50/22* (2013.01); *A61B 5/1172* (2013.01); *A61G 2203/20* (2013.01); *A61G 2203/30* (2013.01); *A61G 2205/10* (2013.01); *A61G 2205/60* (2013.01)

(58) Field of Classification Search
CPC ..... A61B 5/12551; A47C 21/08; A47C 21/00; A61G 2203/20; A61G 2205/60; A61G 2203/30; A61G 7/018; A61G 2205/10; A61G 7/0507; G06F 19/3462; G06F 19/3406; G06Q 50/22
See application file for complete search history.

(56) References Cited

U.S. PATENT DOCUMENTS

| | | | |
|---|---|---|---|
| 4,539,560 | A | 9/1985 | Fleck et al. |
| 4,934,468 | A | 6/1990 | Koerber, Sr. et al. |
| 5,161,274 | A | 11/1992 | Hayes et al. |
| 5,561,412 | A | 10/1996 | Novak et al. |
| 5,636,394 | A | 6/1997 | Bartley |
| 5,699,038 | A | 12/1997 | Ulrich et al. |
| 5,715,548 | A | 2/1998 | Weismiller et al. |
| 5,771,511 | A | 6/1998 | Kummer et al. |
| 5,838,223 | A | 11/1998 | Gallant et al. |
| 5,966,762 | A | 10/1999 | Wu |
| 6,021,533 | A | 2/2000 | Ellis et al. |
| 6,047,424 | A | 4/2000 | Osborne et al. |
| 6,067,019 | A | 5/2000 | Scott |
| 6,133,837 | A | 10/2000 | Riley |
| 6,185,767 | B1 | 2/2001 | Brooke et al. |
| 6,208,250 | B1 | 3/2001 | Dixon et al. |
| 6,279,183 | B1 | 8/2001 | Kummer et al. |
| 6,320,510 | B2 | 11/2001 | Menkedick et al. |
| 6,321,878 | B1 | 11/2001 | Mobley et al. |
| 6,336,235 | B1 | 1/2002 | Ruehl |
| 6,362,725 | B1 | 3/2002 | Ulrich et al. |
| 6,505,368 | B1 | 1/2003 | Ellis et al. |
| 6,584,628 | B1 | 7/2003 | Kummer et al. |
| 6,691,346 | B2 | 2/2004 | Osborne et al. |
| 6,694,549 | B2 | 2/2004 | Perez et al. |
| 6,708,358 | B2 | 3/2004 | Hensley |
| 6,791,460 | B2 | 9/2004 | Dixon et al. |
| 6,876,303 | B2 | 4/2005 | Reeder et al. |
| 6,892,405 | B1 | 5/2005 | Dimitriu et al. |
| 6,957,461 | B2 | 10/2005 | Osborne et al. |
| 6,978,500 | B2 | 12/2005 | Osborne et al. |
| 7,092,376 | B2 | 8/2006 | Schuman |
| 7,171,708 | B2 | 2/2007 | Osborne et al. |
| 7,237,287 | B2 | 7/2007 | Weismiller et al. |
| 7,260,860 | B2 | 8/2007 | Chambers et al. |
| 7,296,312 | B2 | 11/2007 | Menkedick et al. |
| 7,315,535 | B2 | 1/2008 | Schuman |
| 7,319,386 | B2 | 1/2008 | Collins, Jr. et al. |
| 7,325,265 | B2 | 2/2008 | Hornbach et al. |
| 7,330,127 | B2 | 2/2008 | Price et al. |
| 7,389,552 | B1 | 6/2008 | Reed et al. |
| 7,406,731 | B2 | 8/2008 | Menkedick et al. |
| 7,443,302 | B2 | 10/2008 | Reeder et al. |
| 7,451,506 | B2 | 11/2008 | Kummer et al. |
| 7,454,805 | B2 | 11/2008 | Osborne et al. |
| 7,458,119 | B2 | 12/2008 | Hornbach et al. |
| 7,464,605 | B2 | 12/2008 | Douglas et al. |
| 7,469,436 | B2 | 12/2008 | Meyer et al. |
| 7,480,951 | B2 | 1/2009 | Weismiller et al. |
| 7,487,562 | B2 | 2/2009 | Frondorf et al. |
| 7,500,280 | B2 | 3/2009 | Dixon et al. |
| 7,520,006 | B2 | 4/2009 | Menkedick et al. |
| 7,523,515 | B2 | 4/2009 | Allen et al. |
| 7,533,429 | B2 | 5/2009 | Menkedick et al. |
| 7,610,637 | B2 | 11/2009 | Menkedick et al. |
| 7,610,638 | B2 | 11/2009 | Kramer et al. |
| 7,617,555 | B2 | 11/2009 | Romano et al. |
| 7,657,956 | B2 | 2/2010 | Stacy et al. |
| 7,676,862 | B2 | 3/2010 | Poulos et al. |
| 7,676,872 | B2 | 3/2010 | Block et al. |
| 7,690,059 | B2 | 4/2010 | Lemire et al. |
| 7,715,387 | B2 | 5/2010 | Schuman |
| 7,743,441 | B2 | 6/2010 | Poulos et al. |
| 7,757,318 | B2 | 7/2010 | Poulos et al. |
| 7,779,493 | B2 | 8/2010 | Lemire et al. |
| 7,779,494 | B2 | 8/2010 | Poulos et al. |
| 7,784,128 | B2 | 8/2010 | Kramer |
| 8,051,513 | B2 | 11/2011 | Reed et al. |
| 8,155,918 | B2 | 4/2012 | Reed et al. |
| 8,156,586 | B2 | 4/2012 | Reed et al. |
| 2004/0231052 | A1 | 11/2004 | Gladney |
| 2004/0249673 | A1 | 12/2004 | Smith |
| 2005/0203493 | A1 | 9/2005 | Kuroda et al. |
| 2006/0107459 | A1 | 5/2006 | Gladney |
| 2007/0130692 | A1 | 6/2007 | Lemire et al. |
| 2007/0132597 | A1 | 6/2007 | Rodgers |
| 2007/0136102 | A1 | 6/2007 | Rodgers |
| 2007/0180616 | A1 | 8/2007 | Newkirk et al. |
| 2007/0210917 | A1 | 9/2007 | Collins, Jr. et al. |
| 2008/0015903 | A1 | 1/2008 | Rodgers |
| 2008/0021731 | A1 | 1/2008 | Rodgers |
| 2008/0120784 | A1* | 5/2008 | Warner et al. ............ 5/658 |
| 2008/0183910 | A1* | 7/2008 | Natoli ............ A61B 5/00 710/15 |
| 2008/0201429 | A1 | 8/2008 | Barbell et al. |
| 2008/0224861 | A1 | 9/2008 | McNeely et al. |
| 2008/0235872 | A1 | 10/2008 | Newkirk et al. |
| 2009/0091458 | A1 | 4/2009 | Deutsch |
| 2009/0165207 | A1 | 7/2009 | Reed et al. |
| 2009/0165208 | A1 | 7/2009 | Reed et al. |
| 2009/0222988 | A1 | 9/2009 | Reed et al. |
| 2009/0310741 | A1 | 12/2009 | Borghese et al. |
| 2010/0088119 | A1 | 4/2010 | Tipirneni |
| 2012/0157793 | A1* | 6/2012 | MacDonald ............ 600/301 |

OTHER PUBLICATIONS

European Search Report for European Application No. 13160141.1-1651, May 14, 2014, 6 pages.

\* cited by examiner

PATIENT SUPPORT APPARATUS WITH REDUNDANT IDENTITY VERIFICATION

CROSS-REFERENCES TO RELATED APPLICATIONS

The present application claims the benefit of and priority to U.S. Provisional Patent Application Ser. No. 61/613,961, filed Mar. 21, 2012, the disclosure of which is incorporated herein by this reference in its entirety.

BACKGROUND

The present disclosure is related to patient support apparatuses, such as hospital beds, stretchers, and the like. More specifically, this disclosure relates to a patient support apparatus that can verify the identity of a person or an object and/or monitor the person's vital signs.

In healthcare, efforts are often needed to make sure that the patients under care are receiving the proper therapy, medication and/or treatments. To do so, the patient's identity and/or the identity of the person providing or overseeing the therapy, treatment, or medication delivery, may need to be verified. If the patient is to receive medication, the healthcare professional may need to confirm the identity of the medication and/or other details of the patient's prescription and dosing regimen, prior to dispensing the medication to the patient.

SUMMARY

The present application discloses one or more of the features recited in the appended claims and/or the following features which, alone or in any combination, may comprise patentable subject matter:

According to at least one aspect of the present disclosure, a patient support apparatus includes a support frame configured to support a patient in a plurality of positions including a horizontal position; a siderail coupled to the support frame; a first sensing device supported by the siderail; a second sensing device supported by the siderail, the second sensing device being a different type of sensing device than the first sensing device; and a control module in communication with the first sensing device and the second sensing device to verify the identity of a person based on first identity information received by the first sensing device and second identity information received by the second sensing device, the first identity information being different than the second identity information.

In some embodiments, the control module may be in communication with the first sensing device to verify the identity of a medication based on medication identity information received by the first sensing device. In some embodiments, the patient support apparatus may include a display supported by the siderail, where the display may be in communication with the control module to display content relating to a medication whose identity has been verified by the control module and to display content relating to a person whose identity has been verified by the control module. The content relating to the medication may include one or more of dosing information relating to the medication and a digital image of the medication. The content relating to the person may include one or more of prescription information relating to the person and a digital image of the person. The control module may be configured to send data relating to a medication verified by the control module to an electronic medical records system. The control module may be configured to send an alert to a healthcare communication system if the control module is unable to verify the identity of the medication.

In some embodiments, the first sensing device may include a non-biometric sensor and the second sensing device may include a biometric sensor, and the control module may be configured to verify the identity of the person based on non-biometric data received from the first sensing device and biometric data received from the second sensing device. In some embodiments, the first sensing device may include a barcode reader, the second sensing device may include a fingerprint reader, and the control module may be configured to verify the identity of the person based on fingerprint data received from the fingerprint reader and barcode data received from the barcode reader.

In some embodiments, the first sensing device may include a radio-frequency identification (RFID) sensor, the second device may include one of a camera and a microphone, and the control module may be configured to verify the identity of the person based on RFID data received from the RFID sensor and one of facial recognition data received from the camera, barcode data received from the camera, and voice data received from the microphone.

In some embodiments, the control module may be configured to send data relating to a person verified by the control module to an electronic medical records system. The control module may be removably coupled to the siderail. The control module may be configured to send an alert to a healthcare communication system if the control module is unable to verify the identity of the person.

According to at least one aspect of the present disclosure, a patient support apparatus includes a support frame configured to support a patient in a plurality of positions including a horizontal position; a siderail coupled to the support frame; a sensing device supported by the siderail; and a control module in communication with the sensing device to verify the identity of a person based on first identity information received by the sensing device and second identity information received by the sensing device, the first identity information being different from the second identity information. The sensing device may include a camera, the first identity information may include barcode data, the second identity information may include biometric data, and the control module may be configured to verify the identity of the person based on the barcode data and the biometric data.

According to at least one aspect of the present disclosure, a patient support apparatus includes a support frame configured to support a patient in a plurality of positions including a horizontal position; a siderail coupled to the support frame; a docking area defined in the siderail to removably support a barcode reader; and a communication link to couple the barcode reader to a control module of the patient support apparatus when the barcode reader is positioned in the docking area. In some embodiments, the barcode reader may be a handheld device. The barcode reader may be coupled to the docking area by a tether.

In some embodiments, the control module may be configured to receive identification information from the barcode reader and may verify the identity of one or more of a medication, a patient, and a caregiver based on the identification information received from the barcode reader. The control module may be configured to send an alert to a healthcare communication system if the control module is unable to verify the identity of the medication, the patient, or the caregiver.

According to at least one aspect of the present disclosure, a patient support apparatus includes a support frame configured to support a patient in a plurality of positions including a horizontal position; a siderail coupled to the support frame; a pulse oximeter module supported by the siderail, where the pulse oximeter module includes a communication port to connect a pulse oximetry sensor apparatus to the pulse oximeter module; and a display to display pulse oximetry data obtained by the pulse oximetry sensor apparatus from a patient positioned on the patient support apparatus. In some embodiments, the pulse oximeter module may be integrated with the siderail. The pulse oximeter module may be removably coupled to the siderail. The communication port and the display may be positioned on different sides of the pulse oximeter module. The communication port and the display may be positioned on opposite sides of the pulse oximeter module so that when the pulse oximeter module is installed in the siderail, the display faces a caregiver positioned adjacent the patient support apparatus and the communication port faces a person positioned on the patient support apparatus. The display may display pulse oximetry data comprising both graphical and textual data.

In some embodiments, the patient support apparatus may include a control module to communicate the pulse oximetry data from the patient support apparatus to an electronic medical records system. The control module may determine based on the pulse oximetry data whether a person is positioned on the patient support apparatus. The control module may be configured to initiate, modify, or terminate an electronically-controlled function of the patient support apparatus, or to generate an alert or an alarm, in response to the pulse oximetry data. The control module may be configured to verify the identity of the patient based on the pulse oximetry data.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
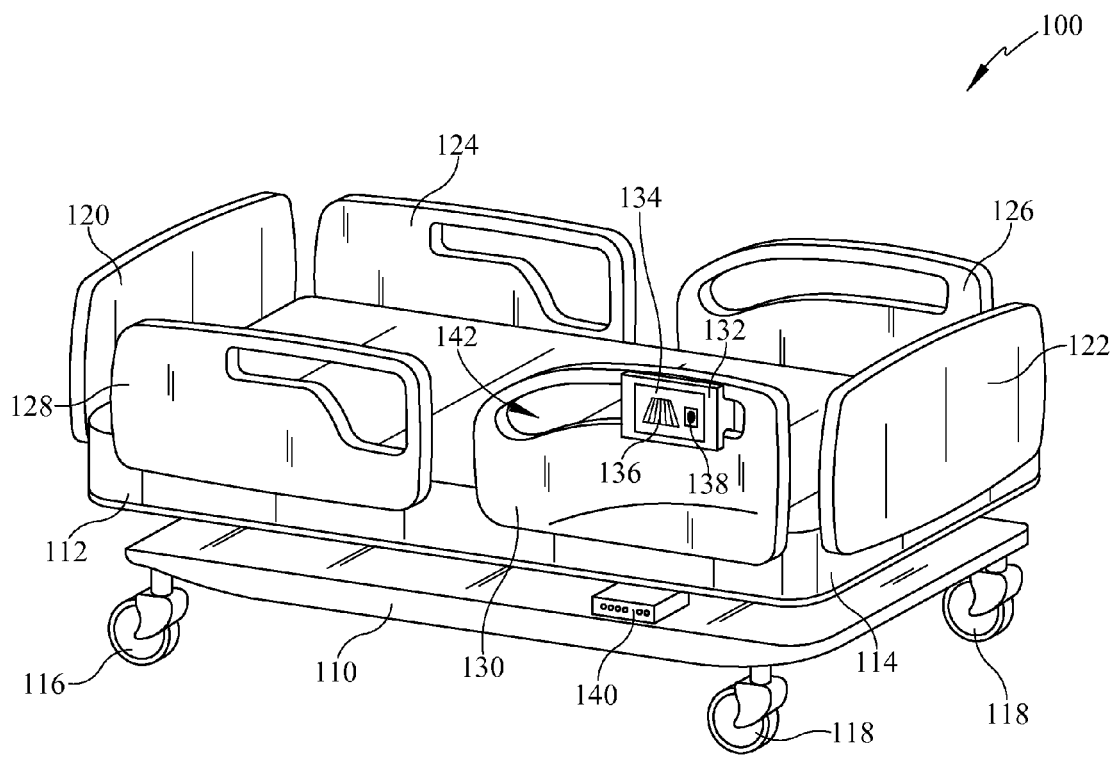
FIG. 1 is a simplified perspective view of at least one embodiment of a patient support apparatus including a siderail with a control unit having sensing devices for identity verification.

Referring now to FIG. 1, an embodiment of a patient support apparatus 100 includes a control unit 132, which has embodied therein an identity verification module 134. The illustrative identity verification module 134 includes a plurality of sensing devices 136, 138 supported thereby. The sensing devices 136, 138 can be used to verify the identity of a person, such as a patient or a caregiver, and/or an object, such as a medication. In this way, redundant identity verification can be performed directly at the point of care, e.g., the location at which the control unit 132 is mounted to the patient support apparatus 100. To do this, each of the sensing devices 136, 138 detects a different form of identifying information, and one or more of the multiple forms of identifying information may be used to authenticate a person or an object. For instance, as illustrated in FIG. 1, the sensing device 136 may be embodied as a non-biometric sensing device such as a barcode reader or radio-frequency identification (RFID) receiver, while the sensing device 138 may be embodied as a biometric sensing device such as a fingerprint sensor. As described in more detail below, other combinations of different types of sensing devices, which are configured to detect different kinds of identifying information, may also be used.

In the embodiment of FIG. 1, the control unit 132 is removably coupled to a siderail 130 of the patient support apparatus 100, in that the control unit 132 may be physically displaced from the siderail and used as a handheld device. As explained further below, however, the control unit 132 and/or other embodiments thereof, such as those shown in the subsequent figures and described below, may be integrated with the siderail (e.g., in a non-removable fashion), or may be similarly removably or fixedly installed in or mounted to another component of the patient support apparatus 100 (such as a headboard 120, a footboard 122, or another siderail 124, 126, 128) or to another architectural structure located at the point of care (a headwall, support column, cart, or point-of-care computer system, for example). In general, any of the embodiments of the control units described herein may include any one or more of the features or functions of any of the other control units herein described, whether or not specifically stated.

The illustrative patient support apparatus 100 is embodied as, for example, a hospital bed, a stretcher, or a similar device that can support a person in a horizontal position and/or one or more non-horizontal positions. The illustrative patient support apparatus 100 is of a type that is typically used in hospitals and/or other facilities in which health care is provided. However, aspects of this disclosure can be applied to any type of person support apparatus or similar structure, including but not limited to beds, mattresses, cushions, tables, stretchers, chairs, wheelchairs and other similar structures, whether or not all of the features of the illustrated patient support apparatus 100 are included in such structure, and whether or not such person support structure includes other features not mentioned herein.

The patient support apparatus 100 has a base 110, which is movably supported by wheels or casters 116, 118 (view of one caster obstructed in FIG. 1). A frame 112 is coupled to and supported by the base 110. In some embodiments, the frame 112 is supported by a lift mechanism, which operates to raise, lower, and tilt the frame 112 relative to the base 110. In some versions of the patient support apparatus 100, a deck may be coupled to and supported by the frame 112. The deck may have a number of sections, some of which may pivot relative to the frame 112 or to each other to, for example, elevate the head section of the bed, lower the foot section of the bed, or a combination thereof (e.g., to attain a chair position). In some embodiments, movement of the frame 112 and/or deck sections may be driven by actuators (not shown), which may be electronically-controlled based on, for example, user and/or sensor inputs.

The frame 112 supports a support surface 114 (e.g., a mattress), which, in turn, may support a patient positioned thereon. The support surface 114 may include a number of air bladders, foam, a combination thereof and/or other suitable materials. In embodiments where the support surface 114 includes air bladders, the inflation and deflation of the air bladders may be electronically-controlled, based on, for example, user and/or sensor inputs.

The electronically-controlled features and functions of the patient support apparatus 100 are managed by a patient support system 900, which is described further below with reference to FIG. 9. Aspects of the system 900 may be implemented at the control unit 132 and/or at a frame- or base-mounted control unit 140, for example. The control unit 140 may include, among other things, computer circuitry for the control of the frame 112, control of the surface 114, and/or network connectivity (including wired and/or wireless connectivity). The electronically-controlled features and functions of the patient support apparatus 100 are powered by a power supply, such as a battery and/or a connector that can connect the patient support apparatus 100 to a supply of electrical current (e.g. a wall outlet).

Figure 2:
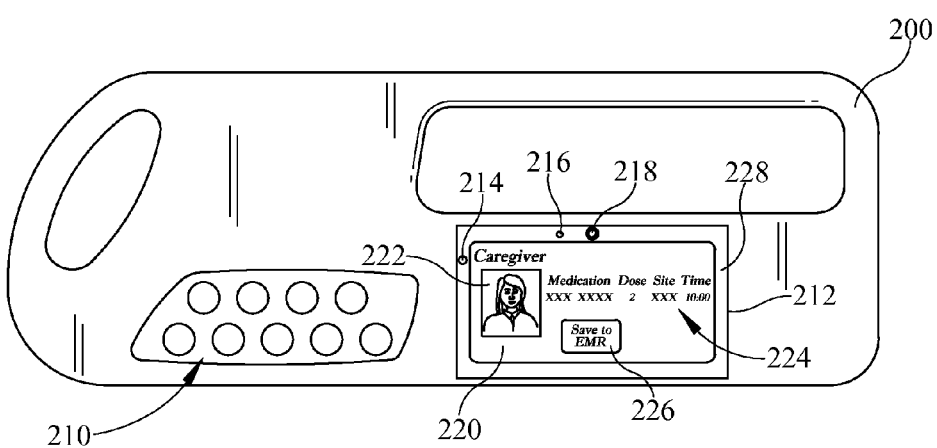
FIG. 2 is a simplified side view of at least one embodiment of another siderail for the patient support apparatus of FIG. 1, including a control unit having sensing devices for identity verification and a display.

Referring now to FIG. 2, a siderail 200 for the patient support apparatus 100 is shown, from the vantage point of a caregiver facing the patient support apparatus 100 if the siderail were installed in the position of the siderail 130 of FIG. 1. The siderail 200 has mounted thereto a number of bed function controls 210, which can be activated by the caregiver or another person to, for example, raise or lower the frame 112 or adjust the inflation parameters of the surface 114. The siderail 200 has installed therein or mounted thereto a control unit 212, which includes a number of sensing devices 214, 216, 218 and a display 220, which are supported by a housing 228. The housing 228 may be integrated with the siderail 200 (e.g., as a single molded piece) in some embodiments. In other embodiments, the housing 228 may be pivotably or removably coupled to the siderail 200. The sensing devices 214, 216, 218 are each configured to capture a different type of identifying information from a person or an object. For instance, in the illustrative control unit 220, the sensing device 214 includes an RFID receiver, which may be used to detect RFID signals transmitted by, for example, an ID badge or bracelet worn by a person, such as a caregiver or a patient. The sensing device 216 includes an acoustic sensor or microphone, which can be used to capture spoken words or phrases uttered by a caregiver or patient. For example, the sensing device 216 may capture a person's speech in response to a prompt for the person to state their name. The sensing device 218 includes an optical sensor or camera, which can be used to capture digital images or representations of, for example, bar codes, facial features, and/or other identifying features of a person or an object.

The illustrative display 220 is embodied as a touch screen display, but may be embodied as any suitable type of interactive display, in other embodiments. In response to inputs received by one or more of the sensing devices 214, 216, 218, information about the person whose identity has been verified by the control unit 212 based on the sensor inputs, and/or information about medication whose identity has been verified by the control unit 212 based on the sensor inputs, is displayed on the display 220. For instance, as shown, a digital image 222 of a caregiver is displayed in response to a determination by the control unit 212 that the caregiver's identity has been verified based on a combination of the sensor inputs (e.g., RFID data transmitted by a tag worn by the caregiver and detected by the RFID sensor 214, voice data captured by the microphone 216, barcode data printed on a tag or ID card carried by the caregiver and scanned by the barcode reader/camera 218, and/or facial recognition data detected by the camera 218). The caregiver's identity may be verified by the control unit 212 executing computer logic to match each of the multiple sensor inputs to corresponding data stored in one or more computer systems, such as a hospital personnel database. Similarly, in the case where the sensing devices 214, 216, 218 may be used to detect identifying information of a patient, the identity data (e.g., bar code, facial features, voice data, and/or RFID data) may be matched against patient information that may be stored in, for example, a hospital admission, discharge, and transfer (ADT) system.

A medication container or packaging having a barcode (e.g., a two-dimensional or three-dimensional bar code or Quick Response (QR) code), may similarly be scanned by the sensing device 218. In such event, the control unit 212 may verify the identity of the medication (e.g., the medication type and dosage form) by matching the medication identification data (e.g., bar code data) received by the sensing device 218 to information stored in a medication database (such as a "global" medication database that may be maintained by an external entity or service, such as a pharmacy or healthcare network). Such a database may be accessed by the control unit 212 via a connection to a hospital communication network and/or a secure connection to an external network such as the Internet. Once the control unit 212 has verified a medication, information such as the medication name and dosage form may be presented to the caregiver on the display 220, so that the caregiver can input corresponding information about a dose of medication actually dispensed to the patient at the point of care. As shown in FIG. 2, the medication information that may be entered by the caregiver at the display 220 may include the actual amount of medication dispensed to the patient (e.g., number of milligrams, number of tablets, etc.), the site or location at which the medication was dispensed to the patient (e.g., the room number and/or bed number), and the date and/or time at which the medication was dispensed to the patient. As shown in FIG. 2, a history of the patient's previous doses of the medication and/or other medications may be obtained from, for example, the patient's electronic medical record, and also displayed. For example, the display may indicate any other doses of medication that the patient has already received on the current day. Once the caregiver has finished entering the patient's current dose information, the information may be saved to the patient's electronic medical record by the activation of a user interface control 226 (e.g., a physical or virtual button, switch, slide, dial, or the like). Activation of the control 226 may cause the patient's current dose information to be stored locally in memory at the patient support apparatus 100 and/or transmitted to, for example, a hospital's electronic medical records (EMR) system, over a hospital communication network.

Figure 3:
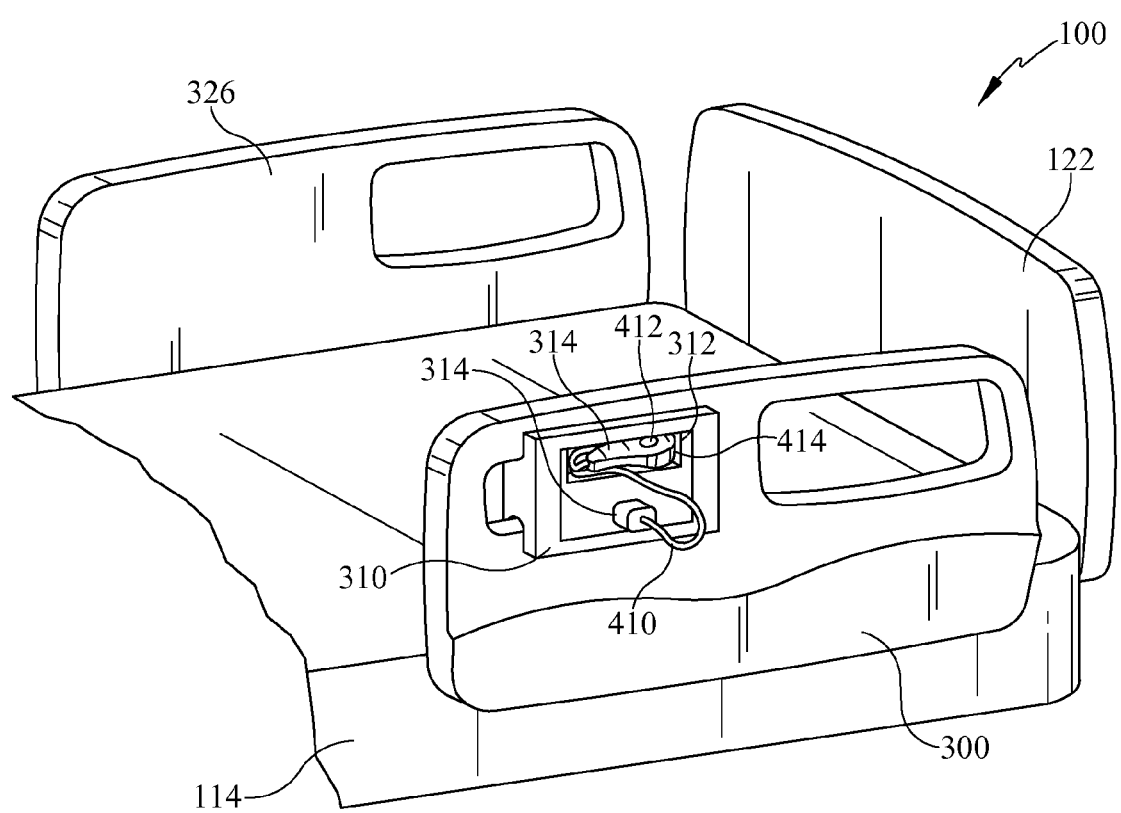
FIG. 3 is a simplified partial perspective view of the patient support apparatus of FIG. 1, including at least one embodiment of a siderail with a control unit having a barcode reader device disposed therein.
Figure 4:
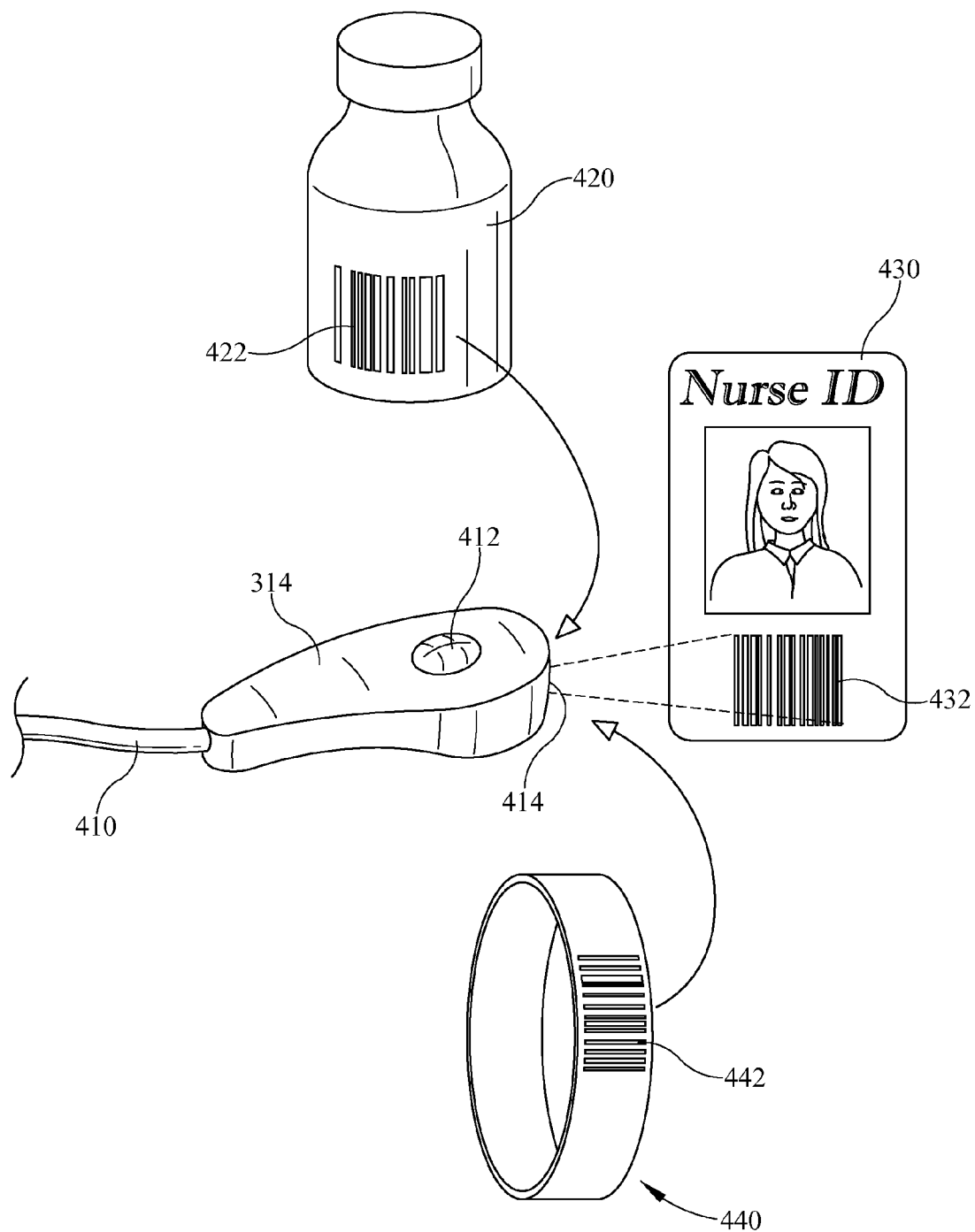
FIG. 4 is a simplified perspective view of at least one embodiment of the barcode reader device of FIG. 3, and showing in relation thereto illustrative objects having labels that may be scanned by the barcode reader device for identity verification.

Referring now to FIGS. 3 and 4, perspective views of a handheld or portable barcode reader 314 are shown. In FIG. 3, the barcode reader 314 is shown coupled to a siderail 300 that may be used in connection with the patient support apparatus 100. Although not specifically shown, the siderail 326 may similarly be configured. In FIG. 4, the barcode reader 314 is shown in relation to objects having labels or tags that may be scanned by the barcode reader 314 for identity verification. In some embodiments, the barcode reader 314 may be a dedicated barcode-scanning device. In other embodiments, the barcode reader 314 may be a multifunctional device such as a mobile computing device (e.g., a smart phone or tablet computer equipped with an integrated camera and barcode-scanning software).

Referring to FIG. 3, the siderail 300 includes a control unit 310 which includes a docking area 312. The docking area 312 is shaped to receive at least a portion of the body of the barcode reader 314, and includes a retainer (e.g., a latch, clip, or detent) to secure the barcode reader 314 therein when the barcode reader 314 is not in use. Although not specifically shown, charging contacts may be supplied within the docking area 312 so that when not in use, the barcode reader 314 may be stored in the docking area 312 in such a way that its charging contacts align with the charging contacts of the docking area 312, so that the barcode reader 314 may be electrically charged by the connection of the charging contacts to the electrical system of the patient support apparatus 100 (e.g., by electrical wiring routed through the siderail 400 to a frame- or base-mounted control unit or power supply).

As shown in FIG. 4, the barcode reader 314 may be coupled to the control unit 310 by a cord or tether 410, which may include electrical wiring or cables, in some embodiments. In such embodiments, the tether 410 may have at its distal end an electrical connector that connects with an electrical port disposed in the docking area 312, for electrical power and/or data communication with the control unit 310. The illustrative barcode reader 314 includes a user control 412 (e.g. a button or switch) and an optical reader or sensor 414 configured to read or scan or capture an image of a bar code label or tag when the sensor 414 is directed at the label and the user control 412 is activated. For instance, the barcode reader 314 may be used to capture barcode data printed on a label 422 attached to a container or package of medication 420, a label 432 attached to an identification badge or tag 430 that may be worn by a person (e.g., a patient or hospital personnel), or a label 442 attached to a bracelet 440 that may be worn by a person (e.g., a patient, caregiver or other hospital personnel). Electrical circuitry transmits the barcode data received by the barcode reader 314 to the control unit 310, either by the electrical contacts or outlet (to which the tether 410 may be connected) located in the docking area 312. In some embodiments, the control unit 310 may include a display similar to that shown in FIG. 2, to display medication or person information associated with the scanned bar code at the siderail 300. In some embodiments, the control unit 310 may communicate the scanned bar code data to the patient support system 900 via an internal bed network, such as a Controller Area Network (CAN), which may then interface with an external system through a hospital communication network to receive therefrom medication and/or person data for display at the control unit 310.

Figure 5:
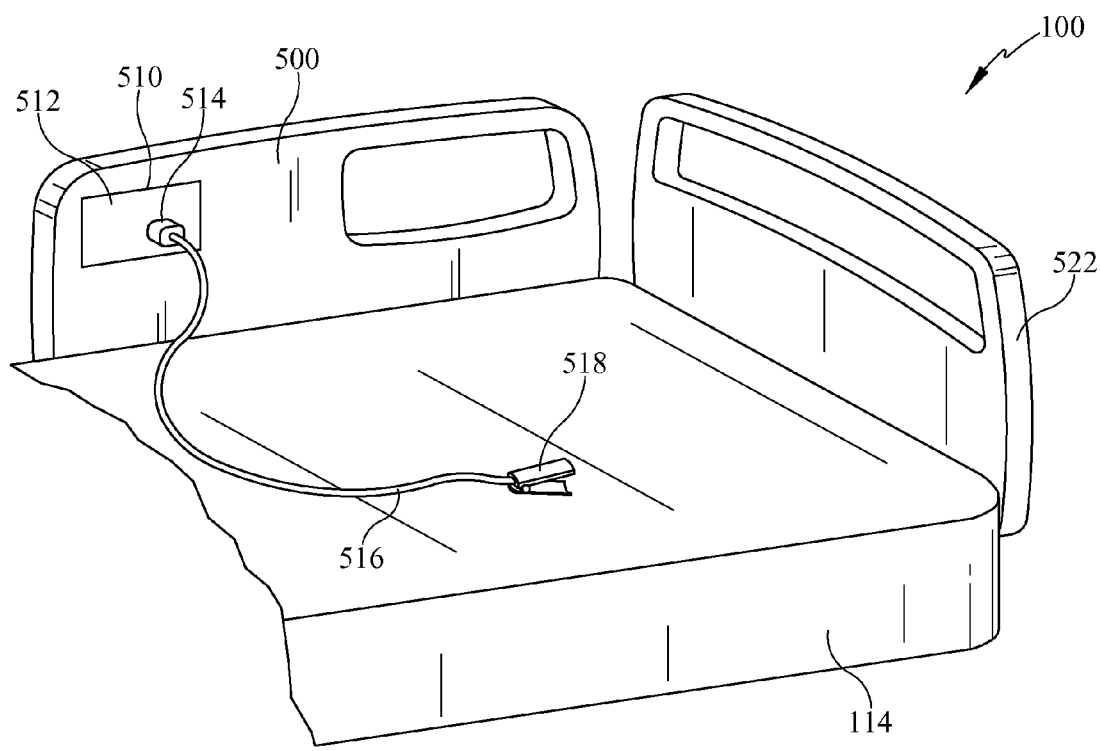
FIG. 5 is a simplified partial perspective view of the patient support apparatus of FIG. 1, including at least one embodiment of a siderail, showing a view of a control unit having a pulse oximeter module and pulse oximetry sensor apparatus, from the vantage point of a patient positioned on the patient support apparatus.
Figure 6:
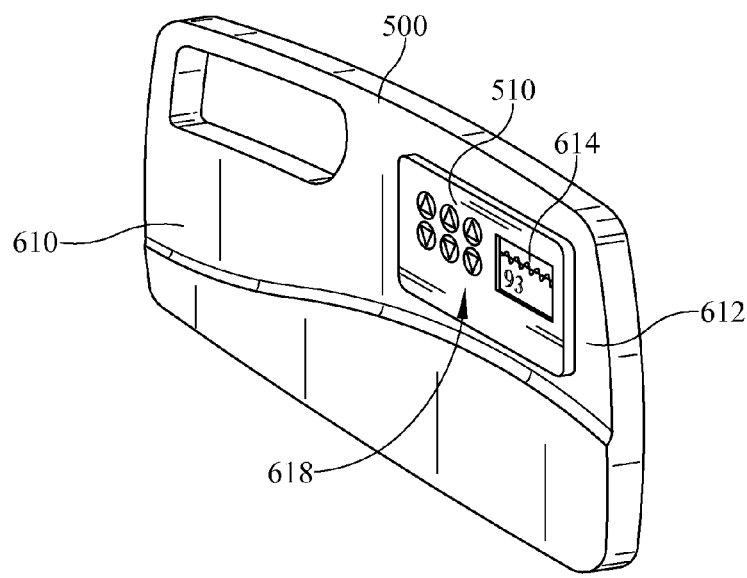
FIG. 6 is a simplified perspective view of the control unit of FIG. 5, showing a view of the control unit from the vantage point of a caregiver positioned adjacent to the patient support apparatus.

Referring now to FIGS. 5 and 6, a control unit 510 is installed in a siderail 500, which may be mounted to the patient support apparatus 100 adjacent an endboard 522, as shown. A patient-facing side 512 of the control unit 510 is shown in FIG. 5; that is, a view of the control unit 510 from the vantage point of a person positioned on the support surface 114 of the patient support apparatus 100. The patient-facing side 512 supports an electrical data communications port to which a communications link 516 (e.g., insulated wiring or cable) connects a vital signs sensing device 518. The sensing device 518 is, in the illustrated embodiment, a pulse oximetry sensor apparatus or "finger clasp." In other embodiments, other types of physiological sensors may be similarly used and connected to the control unit 510. Vital signs data is communicated from the sensing device 518 to the control unit 510, which displays the vital signs data as shown, for example, in FIG. 6. The control unit 510 may communicate the vital signs data to the patient support system 900 via the internal bed network, which may then communicate the vital signs data to another computer system (such as an EMR system), via a secure network connection as mentioned above.

In FIG. 6, a caregiver-facing side 610 of the siderail 500 and the control unit 510 is shown. That is, the side 610 is the view of the siderail 500 that would be seen by a person standing near the side of the patient support apparatus 100 to which the siderail 500 is mounted. The caregiver-facing side of the control unit 510 includes a display 614 and a number of user controls 618. The illustrative display 614 displays a graphical representation and a textual representation of vital signs data detected by the sensing device 518. For instance, as shown, the display 614 shows a graphical depiction and a numerical value indicative of the patient's vital signs data (e.g., blood oxygenation levels) over time, while the patient has their finger inserted in the finger clasp 518. The user controls 618 include physical and/or virtual controls similar to those described above. Some of the user controls 618 may be configured to control one or more of the electronically-controllable features or functions of the patient support apparatus 100. Other controls 618 may control the display 614 to, e.g., change a display parameter such as the time scale or an aspect of the graphical or textual display.

In some embodiments, vital signs data collected by the sensing device 518, or the lack thereof, may be used to determine whether a person is present or absent from the patient support apparatus 100. For instance, if the control unit 510 is receiving vital signs data, it may be inferred that a patient is positioned on the patient support apparatus 100, and vice versa. In response, the control unit 510 may automatically update the configuration of the patient support apparatus 100. For instance, if the control unit 510 infers from the vital signs data that a patient is present on the patient support apparatus 100, the control unit 510 may initiate a patient weighing function, a pressure relief function, or some other electronically-controllable feature or function of the patient support apparatus 100, or may evaluate the vital signs data and issue an alert to inform healthcare personnel if it appears from the vital signs data that the patient may need assistance. Likewise, if the control unit 510 infers from the absence of vital signs data that the patient has exited the patient support apparatus 100, the control unit 510 may terminate or suspend a bed feature or function that was previously in use, or may issue an alert to inform healthcare personnel of the patient's status.

In some embodiments, the vital signs data collected by the sensing device 518 may be used to verify the identity of the patient. For instance, a sampling of such vital signs data captured over time by the sensing device 518 may reveal a vital signs "signature" that can be compared to vital signs signatures of a number of different persons, which may be stored in a hospital or healthcare database. If the patient's vital signs signature is found to match a stored vital signs signature, the patient may be identified. If a match is not found, another form of identification may be requested by the patient support apparatus 100.

Figure 7:
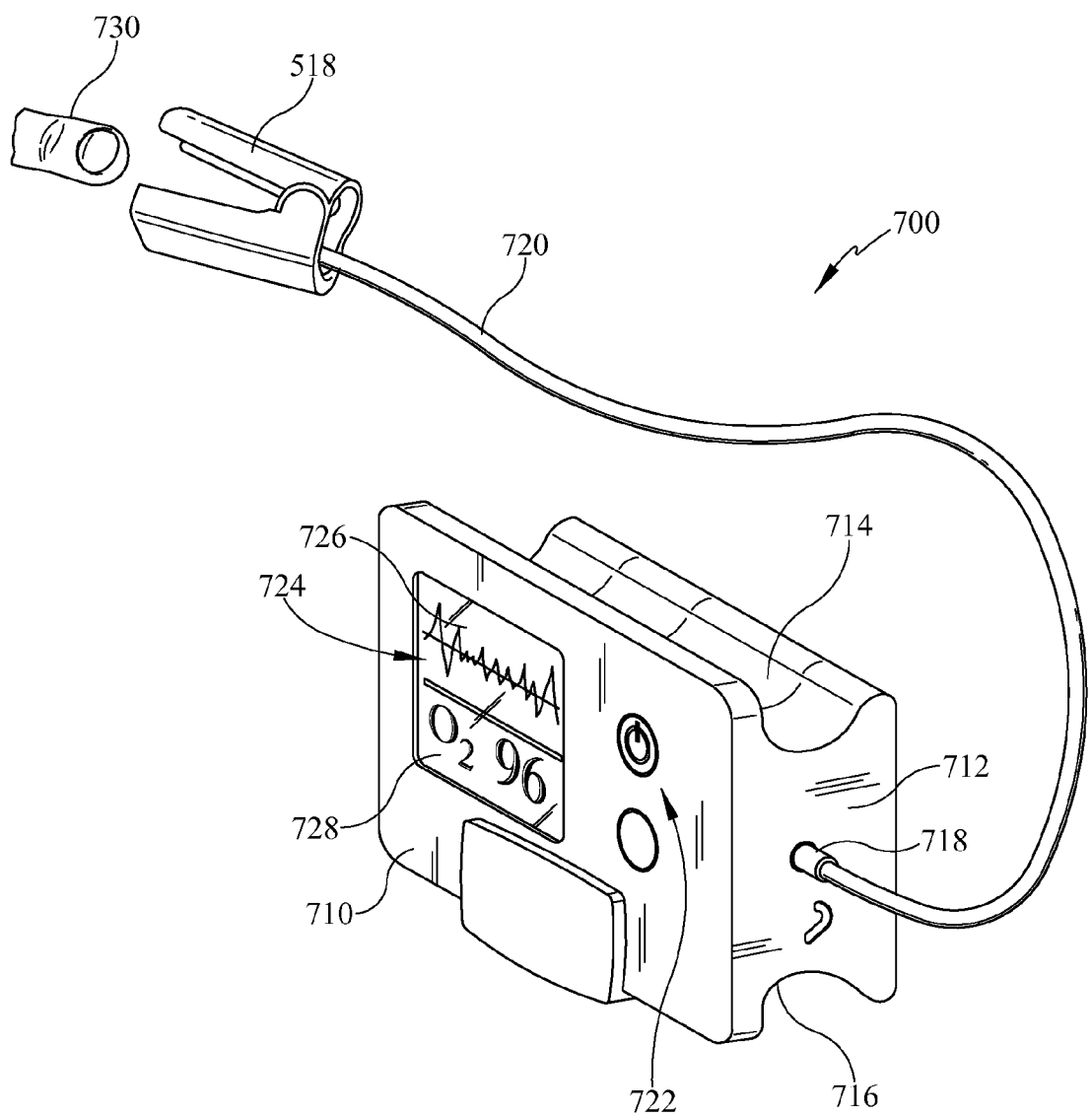
FIG. 7 is a simplified perspective view of at least one embodiment of another control unit for the patient support apparatus of FIG. 1, including a pulse oximeter module and pulse oximetry sensor apparatus.

Referring now to FIG. 7, a control unit 700 includes similar features and functionality as the control unit 510; however, the control unit 700 is embodied as a portable pulse oximeter module that is configured to be removably coupled to a siderail of the patient support apparatus 100. As such, the control unit 700 may be equipped with a wireless transceiver and associated circuitry, in order to communicate vital signs data wirelessly to the patient support system 900. The illustrative control unit 700 is embodied in a housing, which includes a caregiver-facing panel 710, a pair of opposing side panels 712 (view of one panel obstructed), and top and bottom portions 714, 716. The illustrative portions 714, 716 are concavely formed or otherwise configured to cooperate with or be received by corresponding mating portions of a siderail (e.g., the siderail 130) so that the control unit 700 may be removably received and secured within a recess or window of the siderail (e.g., the window 142 of the siderail 130). A data communications port 718 is illustratively supported by the side panel 712, but may be place in any suitable location on the control unit 700 according to the requirements of a particular design. The vital signs sensor or finger clasp 518 is connected to the data communications port 718 by a cable 720. As such, vital signs data (e.g., pulse oximetry data) collected from a patient whose finger is inserted in the finger clasp 518 may be communicated to the control unit 700. The control unit 700 displays graphical 726 and textual/numerical information 728 relating to or representative of the vital signs data collected by the sensing device 518, on a display 724. User controls 722 may be used to configure the display 724 according to the needs of a particular healthcare environment or healthcare situation, in a similar fashion as discussed above.

Figure 8:
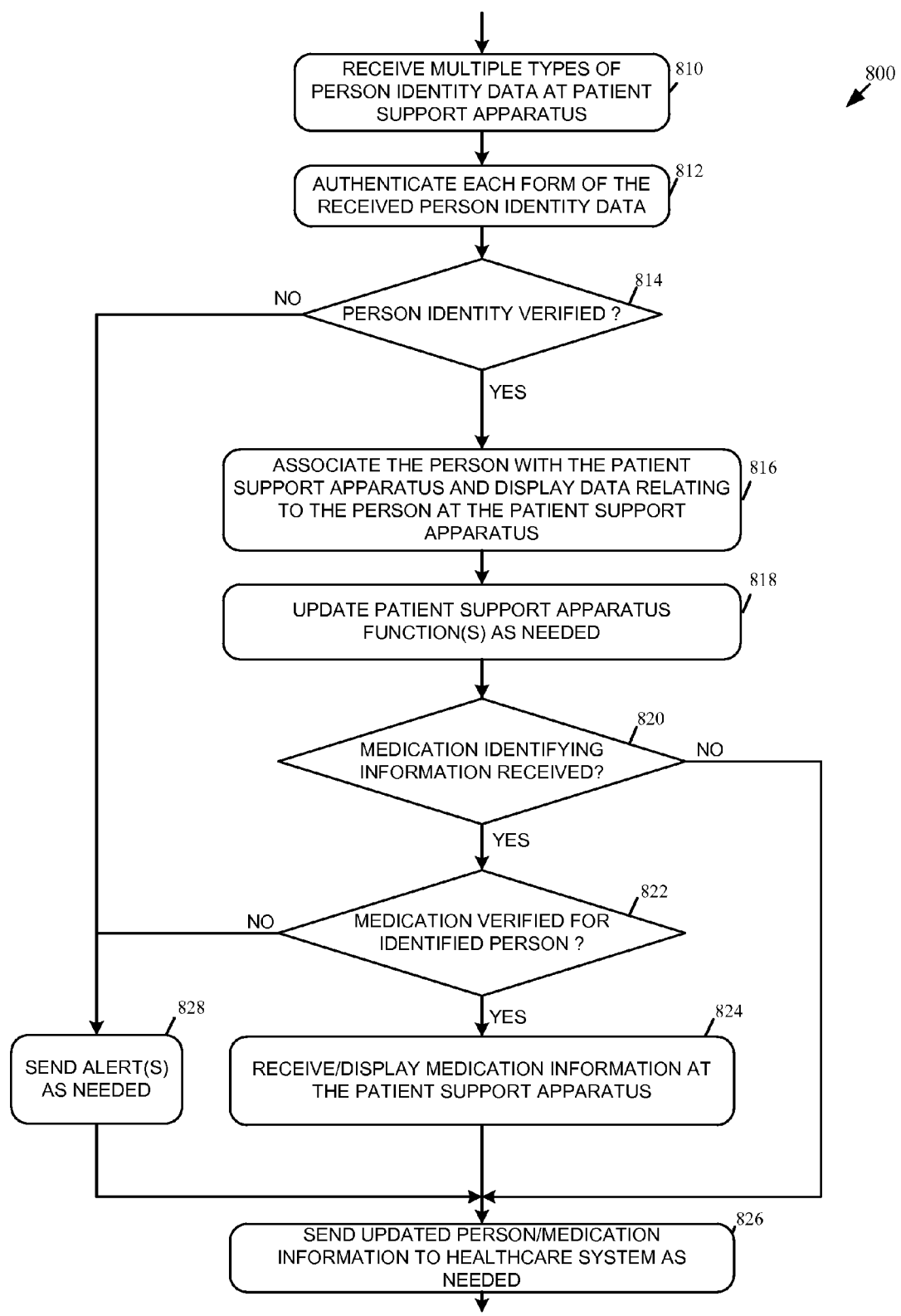
FIG. 8 is a simplified flow diagram of at least one embodiment of a method for handling data communications with sensing devices of a patient support apparatus for identity verification.

Referring now to FIG. 8, a method 800, which may be implemented as executable instructions, modules, routines, or logic units, for example, executed by the system 900, and may be embodied in one or more control modules or units of the patient support apparatus 100, is shown. At block 810, the patient support apparatus 100 receives a combination of at least two different types of person identity data from one or more of the sensing devices described above. For instance, the patient support apparatus 100 may receive bar code data from the bar code reader 136 and fingerprint data from the fingerprint sensor 138. In some embodiments, the patient support apparatus 100 may prompt the user for a secondary type of identity data upon having detected a first, different, type of identity data. For instance, in some embodiments, the patient support apparatus 100 may prompt the user for voice or bar code input upon having received biometric or vital signs data, or vice versa. At block 812, the patient support apparatus 100 authenticates each of the received forms of the person identity data according to its type. For instance, if fingerprint data is received, the patient support apparatus 100 may analyze and/or compare the fingerprint data to a database of stored fingerprint data, which may be accessible to the patient support apparatus 100 by a hospital communication network. Similarly, if voice, barcode, RFID, or facial feature data is received, such data may be analyzed and/or compared to stored samples of that data type. If a match is found (e.g., within reasonable tolerances) for each of the received types of identity data, the patient identity is verified at block 814. Such analyses and comparisons may be carried out by computer logic of one or more modules of the patient support system 900 or, e.g., "in the cloud," at one or more computing devices to which the person support apparatus 100 is communicatively coupled via the hospital communication network 950. If a match is not found for at least two different types of identity data, then additional identifying data may be requested. If the person's identity is not verified by at least two different types of identifying data, then at block 828 the person support apparatus 100 may send an alert to a caregiver or other healthcare personnel, or display the alert at a point-of-care display (such as the display 220 of the control unit 212 of FIG. 2), as needed according to the requirements of a particular design. If the person's identity is verified (e.g., by at least two forms of identifying data), then at block 816, the person's identity is associated with the patient support apparatus and data relating to the person's identity (e.g., name, title, digital image, etc.) may be displayed on a display located at the point of care (e.g., at a siderail of the patient support apparatus 100). If the person whose identity has been verified is a caregiver or other hospital personnel, then the person's identity may be associated with the patient support apparatus 100 for, e.g., healthcare facility workflow monitoring or other reasons. If the person whose identity has been verified is a patient, the person's identity may be associated with the patient support apparatus 100 in order to associate medication, treatment, and/or therapy data generated at the patient support apparatus 100 with the patient's electronic medical record, to track the patient's progress through the healthcare facility, or for other reasons. Data relating to the person's identity may be displayed at the patient support apparatus 100 as shown in FIG. 2, for example.

In some embodiments, at block 818, the configuration or status of an electronically-controllable function or feature of the patient support apparatus 100 may be modified or updated, or an alarm or an alert may be issued (e.g., to a nurse call system) based on the verification of the person's identity, whether such verification is made by biometric sensors, vital signs signatures, or otherwise. For example, if the person is a caregiver, the available bed functions or features may be updated to reflect only those functions or features that the caregiver is able to activate, based on the caregiver's role or access privileges. If the person is a patient, the configuration of the bed functions or features may be configured based on aspects of the patient's medical condition, which may be known to the patient support apparatus 100 through an interface with an EMR system or based on vitals signs data collected at the patient support apparatus 100 from, e.g., a pulse oximeter or other physiological sensor.

At block 820, the patient support apparatus 100 determines whether medication identifying information has been received by one of the identity verification sensing devices. For instance, the patient support apparatus 100 determines whether a barcode scanned by, e.g., the barcode reader 136, 314 relates to a medication. If medication identifying information has not been received, then at block 826, the updated patient information (e.g., the fact that the patient's identity has been verified and any resulting changes to the bed features or functions) may be transmitted to an EMR system or other healthcare system as needed. If medication identifying information has been received at block 820, then at block 822 the patient support apparatus 100 determines whether the medication is verified for the person whose identity was verified at block 814. For instance, if the person whose identity was verified at block 814 is a caregiver, then at block 822 the patient support apparatus 100 determines whether the caregiver is authorized to dispense the medication. To do so, the patient support system 900 may interface with a hospital personnel database, for example, via the hospital communication network 950. If the person whose identity was verified at block 814 is a patient, then the patient support apparatus 100 determines whether the patient's physician has authorized the dispensing of the identified medication to the patient and if so, in what amount. To do so, the patient support system 900 may interface with a hospital EMR system or prescription medication database, for example, via the hospital communication network 950.

If the identified medication is not verified for the identified person (e.g., a caregiver or patient), then the patient support apparatus 100 may send an alert to a healthcare communication system or display a notification at a point of care location, as needed. If the identified medication is verified for the identified person, then at block 824 medication dispensing information may be displayed and/or received at the patient support apparatus 100. For instance, in a first loop of the method 800, a caregiver's identity may be verified at block 814, and at block 822, the caregiver may be approved to dispense a medication identified at block 820. Then, at block 824, information about the medication may be displayed to the caregiver at the patient support apparatus 100. For example, a digital image of the type of medication associated with a barcode received at block 820 may be displayed, so that the caregiver can visually verify that the medication is correct. At block 826, information relating to the caregiver authorization and/or the medication authorization may be sent to an appropriate healthcare system (such as a hospital workflow tracking system) at block 826.

In a second or subsequent loop of the method 800, a patient's identity may be verified at block 814, and at block 822, the patient may be approved to receive the medication identified at block 820. Then, at block 824, the display (e.g., the display 220) may permit the caregiver to enter data relating to the medication actually dispensed and received by the identified patient, as described above. At block 826, the patient support apparatus 100 may send the newly received information about the medication actually dispensed to the patient to the patient's medical record or to a healthcare system (e.g., an EMR system), as needed.

Figure 9:
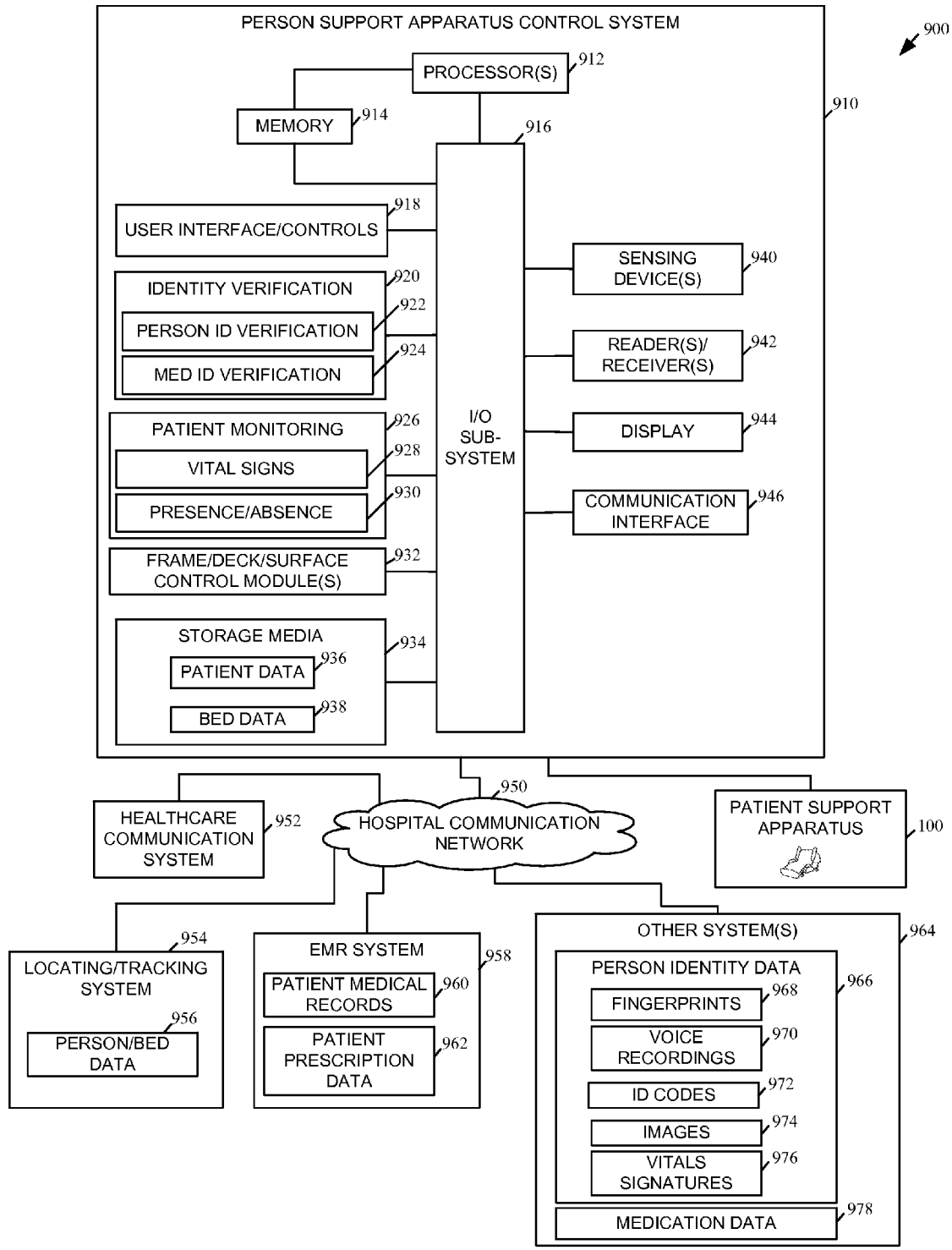
FIG. 9 is a simplified block diagram of at least one embodiment of a control system for a patient support apparatus.

Referring now to FIG. 9, a patient support system 900 including an illustrative patient support apparatus control system 910 is shown in greater detail. As noted above, portions of the patient support apparatus control system 910 may be embodied in different structural units of the patient support apparatus 100. For example, some modules and components of the patient support apparatus control system 910 may be embodied in a siderail- or endboard-mounted control unit, while other modules or components may be embodied in a frame- or base-mounted control unit, which may be in communication with the siderail- or endboard-mounted control unit by a communications network. Such a network may be configured according to a Controller Area Network or Echelon protocol, for example, or according to any other suitable bed network communications protocol.

In the illustrative patient support system 900, the patient support apparatus control system 910 is in communication with the electronically-controllable features and functions of the patient support apparatus 100 as mentioned above, and with one or more other computing systems 952, 954, 958, 964 via the hospital communication network 950. Portions of the patient support apparatus control system 910 may be local to the patient support apparatus 100, however, some portions thereof may be distributed across one or more of the other computing systems 952, 954, 958, 964. For instance, in some cases, identity verification algorithms and/or databases may be located on one or more other computing systems 964.

In general, the patient support apparatus control system 910 includes at least one computing device (such as an embedded device, a desktop computer, a portable computer, a wall-mounted unit, or a server, for example) that includes one or more processors or processor cores (e.g., microprocessors, microcontrollers, digital signal processors, etc.) 912, memory 914, and an input-output subsystem 916. For instance, portions of the control system 910 may be embodied in one or more physical control units of the patient support apparatus 100 and/or any type of computing device including a point of care device such as a "nurse's station" or "patient station" of a nurse-call system, a server, a network of computers, or a combination of computers and/or other electronic devices.

The I/O subsystem 916 typically includes, among other things, an I/O controller, a memory controller, and one or more I/O ports. In some embodiments, the I/O subsystem 916 may include a CAN bus and/or other types of communication links. The processor 912 and the I/O subsystem 916 are communicatively coupled to the memory 914. The memory 914 may be embodied as any type of suitable computer memory device (e.g., volatile memory such as various forms of random access memory).

The I/O subsystem 916 is communicatively coupled to a number of hardware and/or software components including user interface/controls 918 (e.g., any of the user controls described above), an identity verification module 920 (which includes a person identity verification module 922 and a medication identity verification module 924), a patient monitoring module 926 (which includes a vital signs monitoring module 928 and a patient presence/absence monitoring module 930), one or more frame/deck/surface control module(s) 932 (which control features of the bed frame, deck or support surface of the patient support apparatus 100, as mentioned above), one or more machine-readable storage media 934 (which may store patient data 936 and/or bed data 938), one or more sensing devices 940 (e.g., the biometric sensing devices and/or non-biometric sensing devices described above), one or more readers/receiver(s) 924 (e.g., RFID receivers, wireless communication transceivers, etc.), a display 944 (e.g., any of the displays described above), and a communication interface 946.

The storage media 934 may include one or more hard drives or other suitable data storage devices (e.g., flash memory, memory cards, memory sticks, and/or others). In some embodiments, portions of the modules 920, 926, 932 may reside at least temporarily in the storage media 934. Portions of these modules 920, 926, 932 may be copied to the memory 914 during operation of the patient support apparatus control system 910, for faster processing or other reasons.

The hospital communication network 950 may communicatively couple the person support apparatus control system 910 to one or more hospital or healthcare facility computer systems, for example. Accordingly, the communication interface 946 may include one or more wired or wireless network interface cards or adapters, for example, as may be needed pursuant to the specifications and/or design of the particular system 900.

Computing systems in communication with the hospital communication network 950 may include, for example, a healthcare communication system 952 (e.g., a patient-nurse communication system or "nurse call" system), a locating and tracking system 954 (e.g., a system that monitors the location of caregivers, patients, and/or equipment in a healthcare facility), an EMR system 958, and other system(s) 964 (e.g., an admission, transfer and discharge system, hospital workflow system, etc.). The patient support system 900 may include other components, sub-components, and devices not illustrated in FIG. 9 for clarity of the description. In general, the components of the person support system 900 are communicatively coupled as shown in FIG. 9 by electronic signal paths, which may be embodied as any type of wired or wireless signal paths capable of facilitating communication between the respective devices and components.

In more detail, the identity verification module 920 processes identity data received by the sensing devices 940 and/or readers/receivers 942. If the identity data relates to a person, the person identity verification module 922 verifies the received identity data. For example, the person identity verification module 922 may access person identity data 966, and compare the received identity data to corresponding data stored in a person identity database, depending on the data type of the identity data. If the identity data is received from a fingerprint reader, for example, the person identity verification module 922 compares the received fingerprint data to data stored in a fingerprints database 968. Similarly, the person identity verification module 922 compares received voice data to stored voice recordings 970, compares received ID codes (e.g., RFID codes or barcodes) to stored ID codes 972, compares received digital images (e.g., facial features) to stored images 974, and compares received vitals signs signatures to stored vital signs signatures 976, in order to verify a person's identity. Likewise, if the received identity data relates to a medication, the medication identity verification module 924 compares the received identity information (e.g., barcode) to medication data 978, in order to verify the identity of the medication. The identity verification module 920 or portions thereof may be embodied as software stored and executed locally, e.g., at a siderail-mounted control unit of the patient support apparatus, or portions thereof may be distributed across one or more of the other systems 952, 954, 958, 964 connected to the hospital communication network 950.

When a person's identity is verified, the person (e.g., a caregiver or a patient) may be associated with the patient support apparatus 100 as described above. To do this, the identity verification module 920 may communicate with the locating/tracking system 954 to obtain identifying information about the patient support apparatus 100 and create an association between the person identity data and the identifying information for the patient support apparatus 100. Such information about the person and the patient support apparatus 100, and the association therebetween, may be stored in the storage media 934, e.g., in a patient data structure 936 and/or a bed data structure 938.

When a patient's identity is verified, the identity verification module 920 may access or update medical records 960 and/or prescription data 962 that are associated with the identified patient, as described above. Similarly, when a medication is identified, the identity verification module 920 may access or update the prescription data 962.

The patient monitoring module 926 receives data from vital signs monitoring devices such as the pulse oximetry device described above and/or other physiological sensors. As mentioned above, such vital signs data may be used to determine the presence or absence of a patient on the patient support apparatus 100, or to identify the patient by comparison to the vital signs signatures 976. Accordingly, a vital signs monitoring module 928 receives the vital signs data from the physiological sensors 940 and evaluates the comparison of the received data to the stored vital signs signatures 976, to determine whether there is a match. A presence/absence monitoring module 930 monitors the vital signs data or lack thereof and draws therefrom inferences as to whether the patient is present or absent on the patient support apparatus 100. For example, the module 930 may compare the level and/or frequency of the vital signs signals to one or more threshold values or ranges of values and based on that comparison, determine whether the patient is likely present or absent.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory.

Modules, data structures, and the like defined herein are defined as such for ease of discussion, and are not intended to imply that any specific implementation details are required. For example, any of the described modules and/or data structures may be combined or divided into sub-modules, sub-processes or other units of computer code or data as may be required by a particular design or implementation of the system 900.

In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure. Although certain illustrative embodiments have been described in detail above, variations and modifications exist within the scope and spirit of this disclosure as described and as defined in the following claims.

The invention claimed is:

1. A patient support apparatus embodied as a hospital bed comprising:
a support frame configured to support a patient in a plurality of positions including a horizontal position;
an inflatable patient-support surface supported by the support frame;
a siderail coupled to the support frame;
a first sensing device supported by the siderail;
a second sensing device supported by the siderail, the second sensing device being a different type of sensing device than the first sensing device;
bed function controls coupled to the siderail, the bed function controls being useable to raise and lower the support frame and to adjust inflation parameters of the inflatable patient-support surface; and
a control module in communication with the first sensing device and the second sensing device to verify the identity of a person based on first identity information received by the first sensing device and second identity information received by the second sensing device, the first identity information being different than the second identity information, wherein the control module is configured to analyze vital signs sensing data produced by at least the first sensing device to (i) determine a current health state of a patient supported by the support frame and (ii) verify the identity of the patient, wherein the control module initiates at least one electronically-controllable function of the patient support apparatus in response to the vital signs sensing data.

2. The patient support apparatus of claim 1, wherein the control module is in communication with the first sensing device to verify the identity of a medication based on medication identity information received by the first sensing device.

3. The patient support apparatus of claim 2, comprising a display supported by the siderail, wherein the display is in communication with the control module to display content relating to a medication whose identity has been verified by the control module and to display content relating to a person whose identity has been verified by the control module.

4. The patient support apparatus of claim 3, wherein the content relating to the medication comprises one or more of dosing information relating to the medication and a digital image of the medication.

5. The patient support apparatus of claim 3, wherein the content relating to the person comprises one or more of prescription information relating to the person and a digital image of the person.

6. The patient support apparatus of claim 2, wherein the control module is configured to send data relating to a medication verified by the control module to an electronic medical records system.

7. The patient support apparatus of claim 2, wherein the control module is configured to send an alert to a healthcare communication system if the control module is unable to verify the identity of the medication.

8. The patient support apparatus of claim 1, wherein the first sensing device comprises a non-biometric sensor and the second sensing device comprises a biometric sensor, and the control module is configured to verify the identity of the person based on non-biometric data received from the first sensing device and biometric data received from the second sensing device.

9. The patient support apparatus of claim 8, wherein the first sensing device comprises a barcode reader, the second sensing device comprises a fingerprint reader, and the control module is configured to verify the identity of the person based on fingerprint data received from the fingerprint reader and barcode data received from the barcode reader.

10. The patient support apparatus of claim 1, wherein the first sensing device comprises a radio-frequency identification (RFID) sensor, the second device comprises one of a camera and a microphone, and the control module is configured to verify the identity of the person based on RFID data received from the RFID sensor and one of facial recognition data received from the camera, barcode data received from the camera, and voice data received from the microphone.

11. The patient support apparatus of claim 1, wherein the control module is configured to send data relating to a person verified by the control module to an electronic medical records system.

12. The patient support apparatus of claim 1, wherein the control module is removably coupled to the siderail.

13. The patient support apparatus of claim 1, wherein the control module is configured to send an alert to a healthcare communication system if the control module is unable to verify the identity of the person.

14. A patient support apparatus embodied as a hospital bed comprising:
a support frame configured to support a patient in a plurality of positions including a horizontal position;
a siderail coupled to the support frame;
an inflatable patient-support surface supported by the support frame;
bed function controls coupled to the siderail, the bed function controls being useable to raise and lower the support frame and to adjust inflation parameters of the inflatable patient-support surface;
a control module supported by the support frame or the siderail;
a pulse oximeter module supported by the siderail, the pulse oximeter module comprising:
a communication port to connect a pulse oximetry sensor apparatus to the pulse oximeter module; and
a display to display pulse oximetry data obtained by the pulse oximetry sensor apparatus from a patient positioned on the patient support apparatus, wherein the control module is configured to analyze vital signs sensing data produced by at least the pulse oximeter module to (i) determine a current health state of a patient supported by the support frame and (ii) verify the identity of the patient, wherein the control module initiates at least one electronically-controllable function of the patient support apparatus in response to the vital signs sensing data.

15. The patient support apparatus of claim 14, wherein the pulse oximeter module is integrated with the siderail.

16. The patient support apparatus of claim 14, wherein the pulse oximeter module is removably coupled to the siderail.

17. The patient support apparatus of claim 14, wherein the communication port and the display are positioned on different sides of the pulse oximeter module.

18. The patient support apparatus of claim 17, wherein the communication port and the display are positioned on opposite sides of the pulse oximeter module so that when the pulse oximeter module is installed in the siderail, the display faces a caregiver positioned adjacent the patient support apparatus and the communication port faces a person positioned on the patient support apparatus.

19. The patient support apparatus of claim 14, wherein the display displays pulse oximetry data comprising both graphical and textual data.

20. The patient support apparatus of claim 14, comprising a control module to communicate the pulse oximetry data from the patient support apparatus to an electronic medical records system.

21. The patient support apparatus of claim 14, comprising a control module to determine based on the pulse oximetry data whether a person is positioned on the patient support apparatus.

22. The patient support apparatus of claim 14, wherein the control module is configured to initiate, modify, or terminate an electronically-controlled function of the patient support apparatus, an alert, or an alarm, in response to the pulse oximetry data.

23. The patient support apparatus of claim 14, wherein the control module is configured to verify the identity of the patient based on the pulse oximetry data and based on other data.

* * * * *